United States Patent [19]

Guttmann et al.

[11] Patent Number: 4,743,706

[45] Date of Patent: May 10, 1988

[54] PREPARATION OF UNSATURATED ACIDS AND ESTERS BY OXIDATIVE CONDENSATION

[75] Inventors: Andrew T. Guttmann, Maple Heights; Robert K. Grasselli, Chagrin Falls, both of Ohio

[73] Assignee: The Standard Oil Company, Cleveland, Ohio

[21] Appl. No.: 663,822

[22] Filed: Oct. 22, 1984

Related U.S. Application Data

[63] Continuation of Ser. No. 423,771, Sep. 27, 1982, abandoned, which is a continuation of Ser. No. 194,647, Oct. 6, 1980, abandoned.

[51] Int. Cl.$^4$ .......................................... C07C 67/317
[52] U.S. Cl. .................................... 560/214
[58] Field of Search ................. 560/210, 211, 214

[56] References Cited

U.S. PATENT DOCUMENTS

| | | | |
|---|---|---|---|
| 1,722,297 | 7/1929 | Jaeger | 568/470 |
| 1,851,754 | 3/1932 | Craver | 568/472 |
| 1,913,404 | 6/1933 | Meharg et al. | 568/474 |
| 2,467,223 | 4/1949 | Payne | 568/470 |
| 3,014,958 | 12/1961 | Koch et al. | 560/210 |
| 3,654,345 | 4/1972 | Jentsch | 560/210 |
| 3,655,771 | 4/1972 | Tadenuma et al. | 568/470 |
| 4,118,588 | 10/1978 | Fouquet et al. | 560/211 |
| 4,165,438 | 8/1979 | Schneider | 560/211 |
| 4,232,174 | 11/1980 | Statz et al. | 560/214 |

OTHER PUBLICATIONS

Kirk-Othmer, *Encyclopedia of Chemical Technology*, 2nd, vol. 13, p. 339, Interscience, Publ.

*Primary Examiner*—Donald B. Moyer
*Assistant Examiner*—L. Hendriksen
*Attorney, Agent, or Firm*—M. F. Esposito; V. E. Young; L. W. Evans

[57] ABSTRACT

This invention relates to a novel vapor phase process for the production of unsaturated acids and esters, such as acrylic acid and methyl acrylate, by reacting a primary alcohol with a saturated monocarboxylic acid, ester, or anhydride in the presence of oxygen over a solid catalyst.

27 Claims, No Drawings

PREPARATION OF UNSATURATED ACIDS AND ESTERS BY OXIDATIVE CONDENSATION

This is a continuation of application Ser. No. 423,771, filed Sept. 27, 1982, which in turn is a continuation of Ser. No. 194,647, filed Oct. 6, 1980, now abandoned.

BACKGROUND OF THE INVENTION

Preparation of unsaturated acid derivitives from corresponding saturated compounds by condensation with formaldehyde is known. For example, U.S. Pat. No. 3,701,798 disclosed the production of unsaturated acid derivatives through condensation with formaldehyde over catalysts containing rare earth oxides. U.S. Pat. No. 3,014,958 discloses an improvement for making unsaturated esters from formaldehyde and other esters wherein the feed contains more than 7% of the desired unsaturated ester. Catalysts used in this reference are phosphates and mixed oxides.

U.S. Pat. Nos. 3,933,888, 3,578,702 and 4,165,438 all disclose reactions using formaldehyde over various oxide catalysts such as vanadium-phosphorus, metals of the lanthanide series, or metals found in Groups IIA and Group IIIA of the Periodic Table.

It has now been discovered that derivatives of unsaturated acids can be obtained by the reaction of a saturated derivative with methanol and oxygen, over a suitable catalyst, thus eliminating the need for the use of formaldehyde. Since methanol can be made directly from carbon monoxide and hydrogen (synthesis gas), the invention significantly increases the economic incentive for the production of important monomers, such as methyl acrylate, from starting materials easily available from synthesis gas, e.g. methanol, acetic acid, methyl acetate, providing a viable alternative to processes based on petroleum hydrocarbons.

SUMMARY OF THE INVENTION

The invention referred to hereafter as oxidative condensation, may be described as a process for the production of unsaturated acids and esters which comprises reacting in the vapor phase a first reactant selected from the group consisting of saturated monocarboxylic acids, esters and anhydrides, a second reactant selected from the group consisting of primary and secondary alcohols, and oxygen, in the presence of an oxidation catalyst, said catalyst having at least two elements, wherein at least one is a multi-valent metallic element.

The feed to the present invention's process may be a saturated monocarboxylic acid, ester, or anhydride having two to fourteen carbon atoms. It is preferred that acids and esters be utilized. The preferred acids and esters are acetic acid and acetates, and propionic acid and propionates. While these compounds are preferred, esters of other aliphatic acids may also be used.

The alcohol should be a primary or secondary alcohol, including ethanol, n-proponal, n-butanol, and iso-butanol. The preferred alcohol is methanol.

It may be advantageous to use an ether such as dimethyl ether as feed instead of methanol. Both compounds are easily and selectively interconvertible over a variety of dehydration/hydration catalysts, e.g. gamma-alumina. Thus, if desired, dimethyl ether or its mixtures with the methanol may serve as alternate feed equivalents to methanol alone.

The oxygen necessary for the oxidative condensation may be supplied as oxygen or an oxygen-containing gas such as air.

The oxidative condensation is conveniently carried out by mixing the alcohol such as methanol, with the appropriate acid derivative such as methyl propionate, in the desired ratio, vaporizing the mixture, and passing the vapors along with oxygen over a suitable catalyst. If dimethyl ether is used as feed, it may be introduced together with the oxygen and any gaseous diluent, added dissolved in the liquid feed, or introduced both ways. Fixed or fluid bed operation is possible, and inert diluents such as steam or nitrogen may be added.

The reaction temperature may range from 200° to about 500° C., preferably from 300° to 450° C.; the average residence time may be from 2 to about 60 seconds, preferably from 5 to 20 seconds. The molar ratio of the acid derivative to the alcohol may range from 1:10 to 10:1; the molar ratio of oxygen to the alcohol is suitably from 0.2:1 to 10:1.

A wide variety of catalysts are suitable for the oxidative condensation reaction of this invention. The main requirement of the catalyst is to have an oxidation or dehydrogenation function and a condensation/dehydration function. Thus, many oxidation and dehydrogenation catalysts, both acidic and basic, can be used.

In one aspect of the invention, excellent results have been obtained with mixed phosphates having the general formula Tl $A_aB_bC_cPO_x$ where
A = alkali metal, alkaline earth metal, Tl, or mixtures thereof
B = Fe, Co, Ni, V, Cr, Mn, Cu, Ag, Pt, Pd, Rh, Ru, or mixtures thereof
C = Sc, Y, La, rare earth metal, Th, U, Ti, Nb, Si, Ge, Ta, Mo, W, Bi, Sb, Te or mixtures thereof
where
a = 0–1.5;
b = 0.01–3.0;
c = 0–2.0.
x = the number of oxygens required to satisfy the valence requirements of the other elements present.

Preferably the values of a, b and c should be such that the value of $an_a + bn_b + cn_c$ is 1 to 5, where $n_a$ is the valency of the ion or ions from Group A, $n_b$ is the valency of the ion (or ions) from Group B, and $n_c$ is the valency of the ion or ions from Group C.

The catalysts are prepared by methods known in the art; some typical methods of preparation are shown in the examples.

In another aspect of the invention, catalysts containing antimony and vanadium have proved very useful. They have the general formula $$A_aB_bC_cVSb_mO_x$$

where
A = alkali metal, alkaline earth metal, Tl, La, rare earth metal, Th, or mixtures thereof;
B = Cu, Ag, Fe, Co, Ni, Mn, Cr, Nb, Ta, Ti, P, As, Sn, B, U, or mixtures thereof;
C = Mo, W, Te, Bi, or mixtures thereof
a = 0–1;
b = 0–1;
c = 0–1;

m=0.5-40, preferably 3-15, x=the number of oxygens required to satisfy the valence requirements of the other elements present.

Preferably, the value of a+b+c should be equal to or smaller than 2 but less than m.

The catalysts containing V and Sb, as shown above, are conveniently prepared by a redox reaction such as $$V_2O_5 + Sb_2O_3 \rightarrow 2VSbO_4$$

in which pentavalent vanadium is reduced, while the trivalent antimony of $Sb_2O_3$ is oxidized to the pentavalent state. The $V_2O_5$ can be replaced by ammonium metavanadate or other compounds of pentavalent vanadium. Where excess $Sb_2O_3$ is used, such that m>1, such excess will, during the calcination of the catalyst at a high temperature in air, be oxidized to $Sb_2O_4$, $Sb_6O_3$, and/or $Sb_2O_5$, or the like. Alternatively, the excess antimony in compositions with m>1 can be supplied as a compound of pentavalent antimony, e.g., $Sb_2O_5$. In such a case the excess antimony is preferably added after the redox reaction shown above had been completed. Thus, the catalyst compositions contain all or part of the vanadium in an oxidation state of less than 5+, and most of the antimony in the oxidation states of 4+ and 5+. The preparative methods include, for example, heating an intimate mixture of the dry reactants or, preferably, using an aqueous slurry method as illustrated in the examples. Alternatively, the catalysts may be prepared by reducing the pentavalent vanadium (e.g. $V_2O_5$) separately followed by reaction with a compound of pentavalent antimony e.g. $SbCl_5$ or $Sb_2O_5$. In all methods, supports and additional promoting and modifying elements may be added at different stages of the preparation.

Other suitable catalysts include the following:

molybdates, tungstates, vanadates and chromates of various transition elements, optionally promoted with alkali- and alkaline earth metals;

heteropolyoids of molybdenum and/or tungsten and their salts;

mixtures of molybdates with the phosphates and V-Sb catalysts described above;

crystalline aluminosilicates including zeolites X, Y, mordenites, ZSM-series, and the like, suitably exchanged and/or impregnated with alkali metals, preferably K, Rb, and Cs, alkaline earth metals, and other elements such as Fe, Cu, V, Sb, Pt, Pd, Ag, Mo or W.

The catalysts described herein may be used unsupported, but the use of a suitable carrier, such as silica, alumina, amorphous silica-alumina, mixtures of silica and alumina, crystalline aluminosilicates, titania, zirconia, $BPO_4$, $SbPO_4$ natural clays, and the like are often preferred. Good results have been obtained using alumina with the mixed phosphates, and mixtures of alumina and silica with the catalysts containing vanadium and antimony described above. The concentration of the active catalysts on the support may range from about 5 to about 95% by weight.

SPECIFIC EMBODIMENTS

Example 1

A catalyst having the composition 50% $K_{0.4}Th_{0.48}Cu_{0.48}PO_x + 50\%$ $Al_2O_3$ was prepared as follows. A slurry of 44.1 g hydrated alumina (Catapal SB, 85% $Al_2O_3$) in 170 ml $H_2O$ was heated to 70° C. and a solution of 19.4 g $(NH_4)_2HPO_4$ in 50 ml $H_2O$ was added with stirring, followed by the addition of a warm solution of 39.1 g $(Th(NO_3)_4.4H_2O$ and 17.1 g $Cl(NO_3)_2.3H_2O$ in 65 ml $H_2O$, and a solution of 5.9 g $KNO_3$ in 10 ml $H_2O$. The slurry was evaporated to a low volume at about 90° C., then dried at 120°-125° C. The dry material was treated 3 hours at 290° C., 3 hours at 350° C., ground and screened to 20/35 mesh size, and finally calcined 5 hours at 500° C.

Examples 2-10

Following the procedure of Example 1, various promoted copper-phosphate catalysts were prepared as shown in Table I.

The catalysts were charged to a fixed-bed microreactor equipped with a preheat leg, serving as a vaporizer, and immersed in a temperature-controlled salt bath at 330° C. Liquid feed consisting of a mixture of methyl acetate and methanol in a molar ratio of 10:1 was injected by a syringe pump into the reactor, through the preheat leg over a period of 100 minutes. A mixture of 10 vol.% oxygen and 90 vol.% nitrogen was introduced into the reactor through the preheat leg at the same time. The respective flow rates of the liquid and the gaseous feed were such that a reactant ratio methyl acetate/methanol/$O_2$/$N_2$=10/1/0.8/7.2 was obtained, and the average residence time in the reactor was 10 seconds. The reactor effluent was condensed, weighed, and analyzed by gas chromatography. The results of these experiments are shown in Table I.

Examples 11-16

In the same manner as Example 1, catalysts containing phosphorus promoted with iron, chromium, cobalt, silver and molybdenum were prepared and run as per Examples 2-10 at 330° C. with a contact time of 10 seconds. The results of these experiments are shown in Table II.

Example 17

A catalyst having the composition 42% $VSbO_x$, 42% $Al_2O_3$, and 16% $SiO_2$ was prepared as follows. A slurry of 25.9 g $Sb_2O_3$ in 100 ml $H_2O$ was heated to 75° C., and a hot solution of 2.8 g $NH_4VO_3$ in 300 ml $H_2O$ was added with stirring. The mixture was boiled under reflux overnight. The resulting dark-green liquid was mixed with 49.4 g hydrated alumina, and with 40.0 g 40% silica sol. The mixture was stirred in an open beaker, evaporated at 85°-90° C., and dried at 120°-125° C. The dried material was treated 5 hours at 350° C., ground and screened to 20/35 mesh size, and calcined 5 hours at 550° C.

Examples 18-25

In the same manner as Example 17, catalysts containing vanadium-antimony and promoted by potassium, copper, silver, iron, molybdenum and uranium were prepared. Catalysts of these examples were calcined at 550° C., except for Example 19 which was calcined at 650° C.

The catalysts of Examples 17-25 were tested according to the procedure of Examples 2-10 at a temperature of 330° C. and a contact time of 10 seconds. The results are shown in Table III.

Examples 26-29

In the manner previously disclosed, catalysts of the invention were prepared having the composition set forth in Table IV.

Examples 26 and 29 had a support of 50% $Al_2O_3$, while Examples 27 and 28 had a support of 42% $AlO_3$, 16% $SiO_2$.

A feed of methyl proppionate, methanol and oxygen was passed over the catalyst at a ratio of methylpropionate/methanol of 10/1, and a ratio of oxygen/methanol as shown in the Table. The reaction temperature was 330° C., with a contact time as shown. The results are presented in Table IV.

The following example illustrates the use of dimethyl ether as the second reactant in the oxidative condensation with methyl acetate

Example 30

The reactor was charged with a catalyst having the composition 50% $K_{0.4}Ce_{0.58}Cu_{0.58}PO_x$+50% $Al_2O_3$ (see Example 7). The testing procedure was essentially the same as that of Examples 2-10, except that the liquid feed consisted of methyl acetate alone, while the gaseous feed consisted of oxygen, nitrogen, and dimethyl ether. The composition of the gaseous feed and the respective flow rates of the liquid and the gaseous feeds were such that a reactant ratio methyl acetate/dimethyl ether/$O_2$/$N_2$=10/0.5/0.8/7.2 was obtained, and the average residence time in the reactor was 10 seconds. At the reaction temperature of 330° C., 45.2% ppc of methyl acrylate and 4.6% ppc acrylic acid were obtained, resulting in 49.8% ppc to total product. At 350° C. the yields were 82.1% ppc to methyl acrylate and 13.6% ppc to acrylic acid, resulting in 95.7% ppc to total product.

The following example illustrates the use of a molybdate as oxidation catalyst.

Example 31

A catalyst having the composition 50% $Fe_2Mo_{5.4}O_x$ and 50% $Al_2O_3$ was prepared as follows. To a warm slurry of 59 g Catapal SB in 230 ml $H_2O$ there was added a solution of 50.9 g ammonium heptamolybdate in 90 ml $H_2O$, and a solution of 43.1 g $Fe(NO_3)_3.9H_2O$ in 30 ml $H_2O$. The slurry was stirred and evaporated at 90° C., dried at 125° C., treated 3 hours at 290° C., 3 hours at 350° C., ground and screened, then calcined 5 hours at 430° C. When tested according to Examples 2-10, with Me-acetate and methanol in the feed, 24.2% ppc to methyl acrylate and 12.4% ppc to acrylic acid were obtained, resulting in 36.6% ppc to total product.

The following example illustrates the use of a zeolite exchanged with alkali metal and other elements as oxidation catalyst.

Example 32

A sample of commercial Zeolite 13X (sodium form) was exchanged with cesium by conventional treatment with an excess of $Cs_2CO_3$ solution, washing and drying. The dried material was impregnated with Fe and Mo to a total of approximately 8 wt.% by treatment with aqueous solutions of ammonium heptamolybdate and ferric nitrate, evaporating, drying at 125° C. and treated 3 hours at 290° C. This material (12.6 g) was then mixed with 10.5 g 40% silica sol (4.2 g $SiO_2$), dried, ground and screened, then calcined 5 hours at 450° C. This catalyst, when tested according to the procedure of Examples 2-10 gave a yield of 7.3% ppc to methyl acrylate, and 0.2% ppc to acrylic acid.

TABLE I

Reaction of Methyl Acetate With Methanol and Oxygen Over Mixed Phosphates of Copper

| Example | Catalyst | Per Pass Conversion % | | |
|---|---|---|---|---|
| | | Methyl Acrylate | Acrylic Acid | Total |
| 1 | $K_{0.4}Th_{0.48}Cu_{0.48}PO_x$ | 74.9 | 10.9 | 85.8 |
| 2 | $K_{0.4}Th_{0.6}Cu_{0.24}PO_x$ | 64.5 | 6.5 | 71.0 |
| 3 | $K_{0.4}Th_{0.48}Cu_{0.48}V_{0.1}PO_x$ | 61.7 | 4.1 | 65.8 |
| 4 | $K_{0.4}Th_{0.48}Cu_{0.48}Te_{0.1}PO_x$ | 10.4 | 0 | 10.4 |
| 5 | $K_{0.4}Cu_{1.45}PO_x$ | 22.5 | 1.5 | 24.0 |
| 6 | $K_{0.4}La_{0.58}Cu_{0.58}PO_x$ | 66.9 | 3.8 | 70.7 |
| 7 | $K_{0.4}Ce_{0.58}Cu_{0.58}PO_x$ | 89.9 | 12.9 | 102.8 |
| 8 | $K_{0.4}Cr_{0.58}Cu_{0.58}PO_x$ | 41.2 | 11.6 | 52.8 |
| 9 | $K_{0.4}U_{0.725}Cu_{0.725}PO_x$ | 27.0 | 4.3 | 31.3 |
| 10 | $K_{0.4}Bi_{0.58}Cu_{0.58}PO_x$ | 10.8 | 2.1 | 12.9 |

TABLE II

Reaction of Methyl Acetate With Methanol and Oxygen Over Promoted Phosphate Catalysts

| Example | Catalyst | Per Pass Conversion % | | |
|---|---|---|---|---|
| | | Methyl Acrylate | Acrylic Acid | Total |
| 11 | $K_{0.4}Fe_{0.57}PO_x$ | 22.4 | 2.1 | 24.5 |
| 12 | $Th_{0.11}Fe_{0.54}PO_x$ | 19.8 | 2.7 | 22.5 |
| 13 | $K_{0.4}Cr_{0.57}PO_x$ | 15.8 | 1.0 | 16.8 |
| 14 | $K_{0.4}Th_{0.48}Co_{0.48}PO_x$ | 7.5 | 0.0 | 7.5 |
| 15 | $K_{0.4}Th_{0.58}Ag_{0.58}PO_x$ | 53.3 | 1.6 | 54.9 |
| 16 | $K_{0.4}Th_{0.09}Fe_{0.45}Mo_{0.1}PO_x$ | 39.5 | 8.5 | 48.0 |

TABLE III

Reaction of Methyl Acetate With Methanol and Oxygen Over Vanadium-Antimony Catalysts

| Example | Catalyst | Per Pass Conversion % | | |
|---|---|---|---|---|
| | | Methyl Acrylate | Acrylic Acid | Total |
| 17 | $VSbO_x$ | 35.4 | 9.6 | 45.0 |
| 18 | $VSb_5O_x$ | 36.6 | 10.8 | 47.4 |
| 19 | $VSb_5O_x$ | 42.8 | 11.3 | 54.1 |
| 20 | $K_{0.4}VSb_5O_x$ | 39.3 | 5.5 | 44.8 |
| 21 | $K_{0.4}Cu_{0.5}VSb_5O_x$ | 20.3 | 6.0 | 26.3 |
| 22 | $K_{0.4}Ag_{0.5}VSb_5O_x$ | 33.5 | 7.7 | 41.2 |
| 23 | $K_{0.4}Fe_{0.5}VSb_5O_x$ | 33.3 | 6.5 | 39.8 |
| 24 | $K_{0.4}Mo_{0.5}VSb_5O_x$ | 32.5 | 8.5 | 41.0 |
| 25 | $U_{0.5}VSb_5O_x$ | 35.8 | 9.1 | 44.9 |

TABLE IV

Reaction of Methyl Propionate With Methanol and Oxygen Over Various Catalysts

| Example | Catalyst | Contact Time Sec. | $O_2$ MeOH | Per Pass Conversion % | | |
|---|---|---|---|---|---|---|
| | | | | Methyl Methacrylate | Methacrylic Acid | Total |
| 26 | $VSbO_x$ | 6 | 0.4 | 17.5 | 3.0 | 20.5 |
| 27 | $VSb_5O_x$ | 6 | 0.4 | 22.0 | 2.3 | 24.3 |
| 28 | $K_{0.4}VSb_5O_x$ | 10 | 0.8 | 23.3 | 2.5 | 25.8 |
| 29 | $K_{0.4}Fe_{0.5}Ce_{0.47}PO_x$ | 10 | 0.8 | 7.9 | 0.5 | 8.4 |

We claim:

1. A process for the production of unsaturated esters which comprises reacting in the vapor phase at a temperature of 200° C. to 500° C. a first reactant selected from saturated esters and anhydrides having 2 to 14 carbon atoms, a second reactant selected from primary and secondary alcohols and di-alkyl ethers, and oxygen, in the presence of an oxidation catalyst, said catalyst having the empirical formula:

$$A_aB_bC_cPO_x$$

where
- A = alkali metal, alkaline earth metal, Tl, or mixtures thereof;
- B = Fe, Co, Ni, Cr, Mn, Cu, Ag, Pt, Pd, Rh, Ru, or mixtures thereof;
- C = Sc, Y, La, rare earth metals, Th, U, Nb, Si, Ge, Ta, Mo, W, Bi, Sb, Te or mixtures thereof;

where
- a = 0–1.5;
- b = 0.01–3.0;
- c = 0–2.0;
- x = the number of oxygens required to satisfy the valence requirements of the other elements present.

2. The process of claim 1 wherein the first reactant is an ester of acetic acid or propionic acid.

3. The process of claim 1 wherein the alcohol is selected from the group consisting of ethanol, n-propanol, n-butanol, isobutanol and methanol.

4. The process of claim 3 wherein the alcohol is methanol.

5. The process of claim 1 wherein the first reactant is methylacetate and the second reactant is methanol.

6. The process of claim 1 wherein the first reactant is methylpropionate and the second reactant is methanol.

7. The process of claim 1 wherein the first reactant is an ester of a saturated monocarboxylic acid.

8. The process of claim 7 wherein the second reactant is dimethyl ether.

9. The process of claim 1 wherein the first reactant is methyl acetate and the second reactant is dimethyl ether.

10. The process of claim 1 wherein the first reactant is methyl propionate and the second reactant is dimethyl ether.

11. The process of claim 1 wherein A of the oxidation catalyst is an alkali metal.

12. The process of claim 11 wherein member B of the oxidation catalyst is selected from the group consisting of copper, chromium, iron and silver.

13. The process of claim 11 wherein member C of the oxidation catalyst is thorium.

14. The process of claim 11 wherein the alkali metal is potassium.

15. The process of claim 11 wherein the alkali metal is cesium.

16. The process of claim 11 wherein member C of the oxidation catalyst is cerium.

17. The process of claim 11 wherein member C of the oxidation catalyst is one or more elements selected from the group consisting of cerium, lanthanum, thorium, molybdenum, and tungsten.

18. The process of claim 1 wherein the oxidation catalyst has the empirical formula $K_{0.2-06}Ce_{0.45-0.65}Cu_{0.45-0.65}PO_x$.

19. The process of claim 1 wherein the oxidation catalyst has the empirical formula $K_{0.2-0.6}Ce_{0.05-0.2}Fe_{0.4-0.6}Mo_{0.05-0.8}PO_x$.

20. A process for the production of unsaturated esters which comprises reeacting in the vapor phase at a temperature of 200° C. to 500° C. a first reactant selected from saturated esters and anhydrides having 2 to 14 carbon atoms, a second reactant selected from primary and secondary alcohols and di-alkyl ethers, and oxygen, in the presence of an oxidation catalyst, said catalyst having the empirical formula:

$$A_aB_bC_cVSb_mO_x$$

where
- A = alkali metal, alkaline earth metal, Tl, La, rare earth metal, Th, or mixtures thereof;
- B = Cu, Ag, Fe, Co, Ni, Mn, Cr, Nb, Ta, Ti, P, As, Sn, B, U, or mixtures thereof;
- C = Mo, W, Te, Bi, or mixtures thereof;
- a = 0–1;
- b = 0–1;
- c = 0–1;
- m = 0.5–40;
- x = the number of oxygens required to satisfy the valence requirements of the other elements present.

21. The process of claim 20 wherein m = 3–15.

22. The process of claim 21 wherein A of the catalyst is an alkali metal.

23. The process of claim 22 wherein B of the catalyst is selected from the group consisting of iron and copper.

24. The process of claim 22 wherein member C of the catalyst is molybdenum.

25. The process of claim 20 wherein the oxidation catalyst has the empirical formula $VSb_5O_x$.

26. The process of claim 20 wherein the oxidation catalyst has the empirical formula $VSb_{10}O_x$.

27. The process of claim 22 wherein the alkali metal is selected from the group consisting of potassium and cesium.

* * * * *